(12) United States Patent  
Guerquin et al.

(10) Patent No.: US 7,736,298 B2
(45) Date of Patent: Jun. 15, 2010

(54) DEVICE AND PROCESS FOR PREVENTING FEMALE STRESS URINARY INCONTINENCE

(75) Inventors: Bernard Guerquin, 3, Impasse des Roseaux, Saint-Avold (FR) 57000; Rémi Collin, Saint Hilaire sur Erre (FR)

(73) Assignees: B. Braun Medical SAS, Boulogne-Billancourt (FR); Bernard Guerquin, Saint-Avold (FR)

( * ) Notice: Subject to any disclaimer, the term of this patent is extended or adjusted under 35 U.S.C. 154(b) by 0 days.

(21) Appl. No.: 12/066,661

(22) PCT Filed: Sep. 13, 2006

(86) PCT No.: PCT/FR2006/002098

§ 371 (c)(1),
(2), (4) Date: Mar. 13, 2008

(87) PCT Pub. No.: WO2007/031645

PCT Pub. Date: Mar. 22, 2007

(65) Prior Publication Data

US 2008/0228027 A1    Sep. 18, 2008

(30) Foreign Application Priority Data

Sep. 14, 2005    (FR)    ................................. 05 09383

(51) Int. Cl.
*A61F 2/00* (2006.01)
*A61F 13/00* (2006.01)

(52) U.S. Cl. .......................................... 600/30; 600/37

(58) Field of Classification Search ............. 600/29–32
See application file for complete search history.

(56) References Cited

U.S. PATENT DOCUMENTS

| 3,705,575 | A | 12/1972 | Edwards |
| 5,386,836 | A | 2/1995 | Biswas |
| 6,418,930 | B1 * | 7/2002 | Fowler .................... 128/830 |
| 6,679,831 | B1 | 1/2004 | Zunker et al. |
| 2002/0083949 | A1 | 7/2002 | James |
| 2004/0158122 | A1 * | 8/2004 | Guerquin .................... 600/29 |

FOREIGN PATENT DOCUMENTS

| AU | 614 940 B2 | 9/1991 |
| EP | 0 264 258 A2 | 4/1988 |
| WO | 00/36996 A | 6/2000 |

* cited by examiner

*Primary Examiner*—Charles A Marmor, II
*Assistant Examiner*—Carrie Dorna
(74) *Attorney, Agent, or Firm*—Young & Thompson

(57) ABSTRACT

The invention concerns a device for preventing female stress incontinence designed to be arranged in the vagina, comprising a proximal part (12) extending between a free end and a second end, configured to be undeformable under pressure and to be placed in the suburethral region of the vagina, and a distal part (14) extending the second end of the proximal part (12), made of a material reversibly deformable under pressure, and designed to be placed in the subvesical region of the vagina. The invention is characterized in that the distal part (14) delimits a closed outline which receives the weight of the bladder and transforms same into an ascending force acting on the urethra.

20 Claims, 2 Drawing Sheets

DEVICE AND PROCESS FOR PREVENTING FEMALE STRESS URINARY INCONTINENCE

This invention relates to a device for preventing female stress urinary incontinence, designed to be arranged longitudinally in a vagina.

Devices for preventing female stress urinary incontinence are already known. For example, the document U.S. Pat. No. 5,785,640 describes a device that is inserted deeply into the subvesical region of the vagina so that its front end exerts pressure at the location of the vesical collar. The suburethral part of the vagina remains virtually free.

The document U.S. Pat. No. 5,386,836 describes an intravaginal device that comprises a ring that bears one or two projections going beyond the ring in a direction that makes an angle of 90 to 135° with the plane of the ring; the projections are designed to support the vesical collar. Consequently, the projections apply pressure on both sides of the vesical collar or on the vesical collar, but they do not penetrate the suburethral region since they are limited to the vesical collar.

The document U.S. Pat. No. 6,679,831 describes a device for preventing female stress urinary incontinence that comprises an internal elastic element and a non-absorbent material. The elastic element is designed to give to the device, after it has been extracted from an applicator, a shape that expands at the vesical collar, which is thus subjected to local pressure. This document describes devices that can assume M or Y shapes as well as shapes that have a circular portion that is extended by a rod. In all the embodiments, the widest part contains the elastic element and is designed to be the innermost part; when it expands, after it leaves the applicator, it exerts a localized pressure at the vesical collar. These devices are not designed to penetrate beyond the vesical collar.

The document EP-1 279 381 describes a device for preventing female stress urinary incontinence that comprises a proximal part and a distal part that extends it. In this document, the distal part is designed to penetrate the suburethral part of the vagina and to expand it. This document does not provide any indication on the interaction of the bladder and the distal part. In this device, the proximal part is designed to be found in the suburethral part of the vagina and to exert pressure on the urethra, between the vesical collar and the urinary meatus, preferably over a certain length. The distal part has as its role to position the proximal part along the suburethral part of the vagina so that it exerts pressure on the urethra.

The devices of the first two documents, as well as numerous others, have the drawback of permanently lifting the urethra-vesical junction, whereas the stress urinary leaks happen only for short periods. This constant pressure can create an anatomical deformation that can itself be the cause of discomfort and even pain. In addition, the contact is extremely localized over a very small region of the wall. In addition, in the case of the first document, a very localized rear contact is also established and can itself be the cause of discomfort and even pain.

In addition, the positioning, in the case of the first two documents, is very difficult to accomplish; if the device is too embedded, it is ineffective, and if it is not embedded enough, it may create discomfort, and even pain, and can even make it impossible to urinate.

In addition, in the case of the first document, the contact at the vesical collar is carried out on both sides of the urethra and not directly against the latter.

The device of the last aforesaid document EP-1 279 381 has numerous advantages, in particular the fact of being effective thanks to its action over an extended part of the length of the urethra.

An improvement to the device of the document EP-1 279 381, which makes it possible to profit dynamically by the conditions that are suitable for the user, and more specifically filling the bladder to adapt its own action, has now been discovered.

It is easily understood that the urinary incontinence incidents are more frequent when the bladder is full than when it is empty. According to the invention, thanks to the use of a distal part with closed contour, delimiting an extended surface of action of the weight of the bladder, this weight acts on this distal part based on the state of filling of the bladder; this distal part then transmits, by a lever effect, a force that is all the greater the more full the bladder, in the proximal part that consequently acts on the urethra.

One obvious advantage of this characteristic is that since the device adapts automatically to the filling state of the bladder, it creates only a small discomfort, primarily when the bladder is not very full.

More specifically, the invention relates to a device for preventing female stress urinary incontinence that is designed to be arranged longitudinally in the vagina and that comprises a proximal part (12) that extends between a first free end and a second end, produced so as to be essentially non-deformable under pressure and designed to be placed in the suburethral region of the vagina over a significant length of this region, and a distal part (14) that extends the second end of the proximal part (12), made of a material that is deformable under pressure in a reversible manner and designed to be placed in the subvesical region of the vagina, whereby the distal part (14) delimits a closed contour. Such a closed contour itself delimits an extended surface for application of the weight of the bladder.

Preferably, the proximal part extends over at least one-third the length of the suburethral region, and, very advantageously, over approximately two-thirds of the length of the suburethral zone.

Preferably, the closed contour of the distal part has a ring shape.

It is advantageous that the thickness of the distal part is smaller on the distal end than on the side of the proximal part.

Preferably, the distal part is elastically deformable at least between an operating position in which it has a rounded shape and an installation position in which its lateral parts are clamped close to one another in the extension of the proximal part.

Preferably, the proximal part has a core that is made of a hard material and is encased by a flexible covering that is made of a biocompatible material. The core advantageously has the shape of a tube section, and the proximal part preferably forms a cavity that empties into the first end.

The proximal part preferably has a cylindrical or tapered shape.

Preferably, the device has a length of between 7 and 9 cm, and the distal part has a width of between 4 and 5.5 cm.

Preferably, the device also comprises a device for its removal, mounted at the first end of the proximal part.

Preferably, the part of the device that forms the transition between the proximal part and the distal part is elastically deformable.

The invention also relates to a process for preventing female stress urinary incontinence that comprises the transformation, by a lever effect, of the weight of the bladder into an upward force acting on the urethra, by articulation at a location of the vaginal cavity close to the vesical collar.

Other characteristics and advantages of the invention will emerge better from the following description of embodiments, done with reference to the accompanying drawings, in which.

Figure 1:
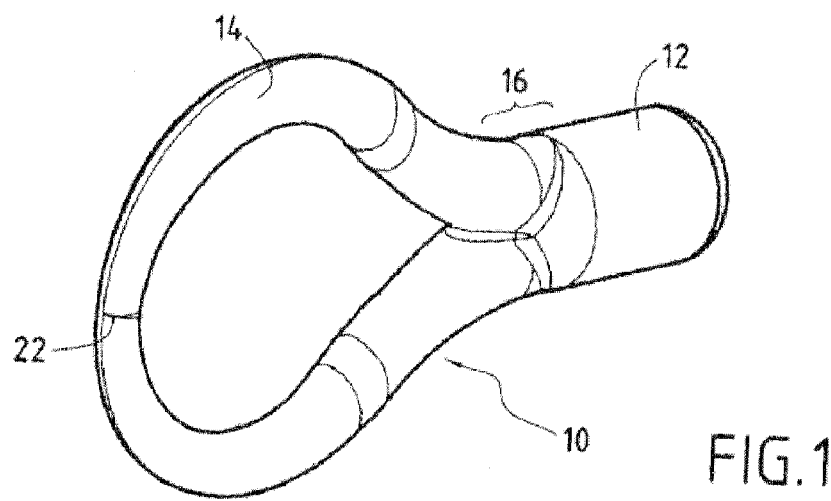
FIG. 1 is a perspective view of a device for preventing female stress urinary incontinence according to the invention.
Figure 2:
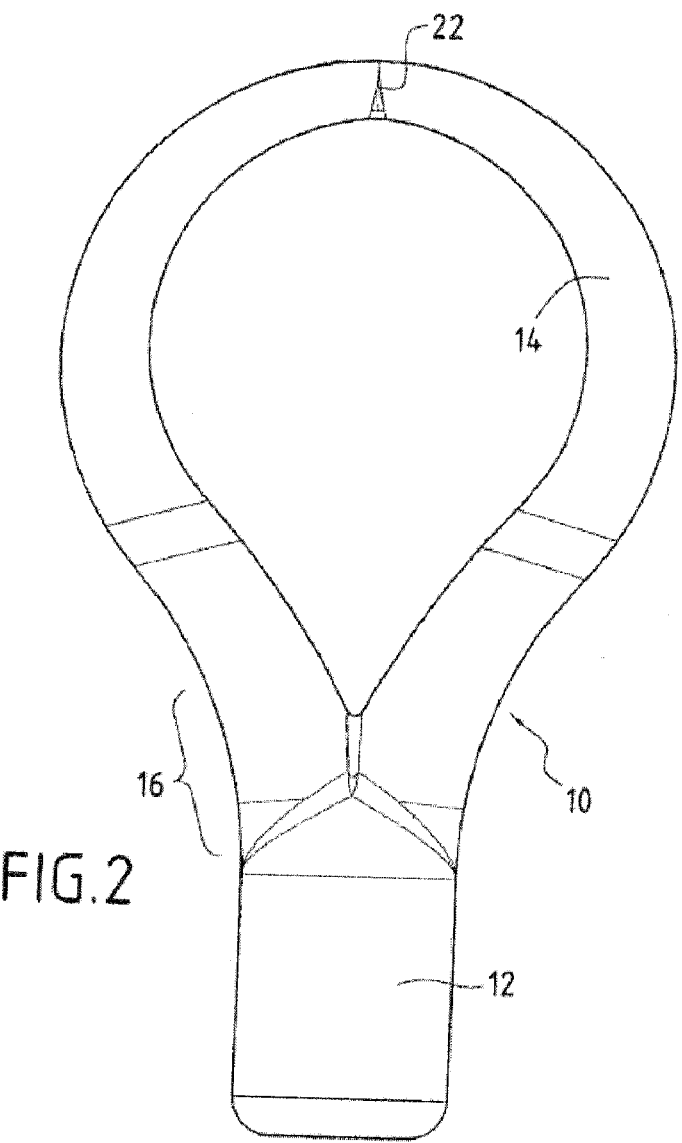
FIG. 2 is a plan view of the device of FIG. 1.
Figure 3:
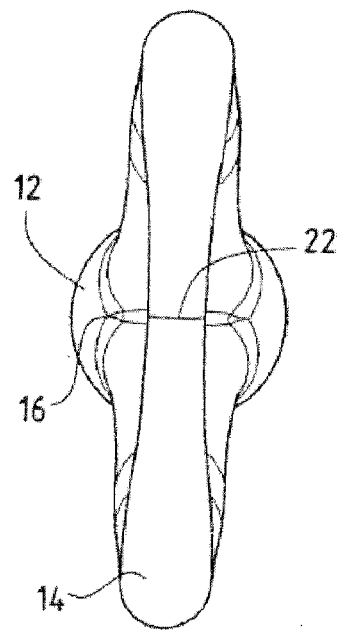
FIG. 3 is an end view of the device of FIG. 1.

FIG. 1 is a perspective view of a device for preventing female stress urinary incontinence according to the invention. This device comprises a proximal part 12 and a distal part 14 virtually in the shape of a ring, with a transition that is designated by the reference 16. The device 10 comprises, in its proximal part 12, a virtually rigid element 18, advantageously in the form of a tube section that is equipped with, for example, a crosspiece that makes it possible to attach an extraction thread.

Figure 4:
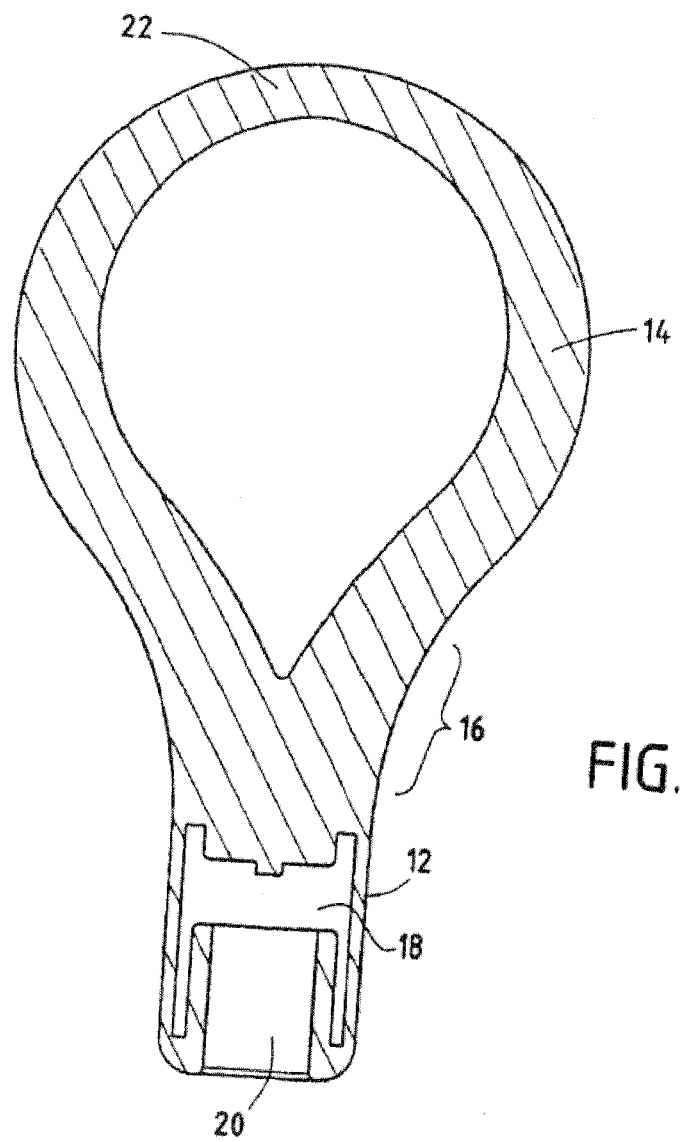
FIG. 4 is a median sectional drawing of the device of FIGS. 1 to 3, showing an advantageous characteristic of the invention.

It is noted in FIG. 4 that the rigid element 18 is encased in the material of the device 10, and it is exposed only by an orifice 20, such that it is never in contact with tissues of the body into which the device is placed. Aside from the rigid element 18, the entire device 10 is formed by a flexible biocompatible material, for example styrene-butadiene-ethylene-styrene (SBES).

The distal part 14, which provides a racket shape with the proximal part, has two lateral parts that meet at a peak 22. It is advantageous that the thickness of the distal part 14 gradually decreases from the transition part 16 to the end 22. In this way, the distal part can be easily deformed, primarily in the vicinity of the end 22; for example, the two lateral parts of the distal part 14 can move toward one another by providing a tapered shape that facilitates the insertion into the suburethral part of the vagina, even in the absence of an applicator. In addition, this insertion ensures a suitable automatic positioning of the device; actually, by moving away from one another, the lateral parts pull the proximal part toward the inside until they rest on the lateral walls of the vagina, because the latter expands from the outside to the inside.

Furthermore, whereby the vagina is wider rather than more vertical in its deep part, the device has a tendency to position itself by rotation, even if the lateral parts of the distal part 14 are introduced with a vertical orientation and not a horizontal orientation.

It is possible, however, to use an applicator in which the distal part 14 is clamped, the entire device being held in a hollow cylinder whose inside diameter is virtually equal to the outside diameter of the proximal part 12.

Figure 5:
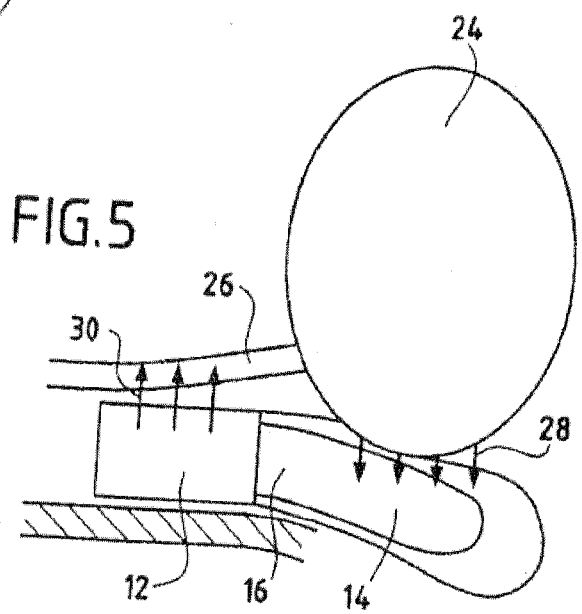
FIG. 5 is a diagram that illustrates the operation of the device according to the invention.

FIG. 5 indicates how the device according to the invention acts after it has been put into position. In this figure, the bladder 24 and the urethra 26 have been shown diagrammatically. When the bladder fills, it exerts pressure on the upper vaginal wall, as indicated by the arrows 28. This pressure is applied in a manner distributed over the distal part 14, which tends to move downward. This downward movement of the distal part 4 is transmitted, by a lever effect, to the proximal part that undergoes an upward force 30 toward the urethra 26. Actually, the transition part 16 is approximately at the vesical collar, and it is virtually in permanent contact with the upper and lower vaginal walls; it thus constitutes a point of articulation that allows the transformation of the downward force 28 into an upward force 30. Thanks to the elasticity of the flexible material of the device 10, this action is carried out gradually and without pain.

It is easily imagined that when the bladder is empty or almost empty, the force 28 is weak although the proximal part 12 exerts a small force 30 on the urethra 26. However, since the bladder is empty, it not very likely that stress causes urinary incontinence. In addition, when laughing or coughing, the abdominal force is exerted in a manner that is virtually identical to the force 28 and causes the projection of the proximal part 12 against the urethra, for a fraction of a second, and prevents incontinence even in this case.

When the bladder is full, all its weight is transmitted by the upper vaginal wall to the distal part 14 that transmits this force elastically to the proximal part whose action on the urethra 26 is multiplied. Actually, it is noted that the lever arm of the distal part 14 is at least double that of the proximal part 12. Consequently, when the bladder is full, the effect of the proximal part of the urethra 26 is more than doubled.

This intense action is limited to times when the bladder is full. When the latter is virtually empty, the force that is exerted in a permanent manner on the urethra 26 can be very small and can therefore cause neither discomfort nor pain.

In a first embodiment, the proximal part 12 has a length of about 20 mm, and the device has a total length of 76 mm, whereby the width of the distal part is about 43 mm. The diameter of the proximal part is 15 mm.

In a second example, the proximal part has a length of about 23 mm, and the device has a total length of 88 mm. The distal part has a width of about 52 mm.

In its two examples, the flexible material is styrene-butadiene-ethylene-styrene (SBES), and the rigid core that is formed by the tube section is polyethylene.

The invention claimed is:

1. A device for preventing female stress urinary incontinence that is designed to be arranged longitudinally in the vagina, comprising:
    a proximal part that extends between a first free end and a second end, produced so as to be essentially non-deformable under pressure and designed to be placed in the suburethral region of the vagina over a significant length of this region, and
    a distal part that extends the second end of the proximal part, made of a material that is deformable under pressure in a reversible manner and designed to be placed in the subvesical region of the vagina, the distal part comprising two lateral parts that connect at a distal end of the distal part to delimit a closed contour adapted to support the weight of the bladder, wherein when the device is positioned in the vagina the two lateral parts can move away from one another and the movement of the two lateral parts moving away from one another pulls the proximal part toward the inside of the vagina until the two lateral parts rest on the walls of the subvesicular region of the vagina.

2. The device according to claim 1, wherein the proximal part extends over at least one-third of the length of the suburethral region.

3. The device according to claim 2, wherein the proximal part extends over approximately two-thirds of the length of the suburethral region.

4. The device according to claim 1, wherein the closed contour of the distal part has a ring shape.

5. The device according to claim 4, wherein the thickness of the distal part is smaller at the distal end than the side of the proximal part.

6. The device according to claim 1, wherein the distal part is elastically deformable at least between a position of operation in which it has a rounded shape and an installation position in which its lateral parts are clamped close to one another in the extension of the proximal part.

7. The device according to claim 1, wherein the proximal part comprises a core made of a hard material that is encased by a flexible covering made of a biocompatible material.

8. The device according to claim 7, wherein the core comprises a tube section, and the proximal part forms a cavity that empties into the first end.

9. The device according to claim 1, wherein the device has a length of between 7 cm-9 cm, and the distal part has a width of between 4 cm-5.5 cm.

10. The device according to claim 1, further comprising a second device for removal of the device mounted at the first end of the proximal part.

11. The device according to claim 1, further comprising an elastically deformable transition part that forms a transition between the proximal part and the distal part.

12. The device according to claim 1, wherein the proximal part has a cylindrical shape or a tapered shape.

13. A method for preventing female stress urinary incontinence in a human, comprising the steps of:
positioning the device of claim 1 in the vagina;
applying pressure from the weight of the bladder to the distal part of the device;
distributing the pressure over the distal part to move the distal part in a downward direction;
transmitting the downward movement of the distal part, by a lever effect, to the proximal part of the device, wherein the proximal part then applies force in an upward direction against the urethra.

14. The method of claim 13, wherein the pressure from the weight of a full bladder is greater than the pressure from the weight of an empty bladder.

15. The method of claim 13, wherein the pressure applied to the distal part is directly correlated to the weight of the bladder.

16. The method of claim 13, wherein the force applied by the proximal part to the urethra is directly correlated to the weight of the bladder.

17. The method of claim 13, wherein the device is positioned longitudinally in the vagina.

18. The device of claim 1, wherein in the distal part, the material that is deformable under pressure in a reversible manner is styrene-butadiene-ethylene-styrene (SBES).

19. The device of claim 1, wherein the proximal part comprises a rigid polyethylene core encased by styrene-butadiene-ethylene-styrene (SBES).

20. The device of claim 19, wherein the entire device is formed by the rigid polyethylene core and styrene-butadiene-ethylene-styrene (SBES).

\* \* \* \* \*